United States Patent [19]

Lazzara et al.

[11] Patent Number: 5,702,346
[45] Date of Patent: *Dec. 30, 1997

[54] DENTAL IMPLANT FIXTURE FOR ANCHORAGE IN CORTCAL BONE

[76] Inventors: Richard J. Lazzara, 1814 N. "R" St., Lake Worth, Fla. 33460; Keith D. Beaty, 245 Miramar Way, West Palm Beach, Fla. 33405

[*] Notice: The term of this patent shall not extend beyond the expiration date of Pat. Nos. 5,695,336 and 5,709,547.

[21] Appl. No.: 601,453

[22] Filed: Feb. 14, 1996

Related U.S. Application Data

[63] Continuation of Ser. No. 222,928, Apr. 5, 1994, abandoned, which is a continuation of Ser. No. 845,138, Mar. 3, 1992, Pat. No. 5,364,268.

[51] Int. Cl.$^6$ .................................................. A61C 8/00
[52] U.S. Cl. .................................... 433/173; 433/174
[58] Field of Search ................................. 433/173, 174, 433/175, 176

[56] References Cited

U.S. PATENT DOCUMENTS

| | | |
|---|---|---|
| 2,112,007 | 3/1938 | Adams . |
| 3,067,740 | 12/1962 | Haboush . |
| 3,488,779 | 1/1970 | Christensen . |

(List continued on next page.)

FOREIGN PATENT DOCUMENTS

| | | |
|---|---|---|
| 0 111134 | 6/1984 | European Pat. Off. . |
| 0 126624 | 11/1984 | European Pat. Off. . |
| 0 139052 | 5/1985 | European Pat. Off. . |
| 0 216031 | 4/1987 | European Pat. Off. . |
| 0 237505 | 9/1987 | European Pat. Off. . |
| 0 288702 | 11/1988 | European Pat. Off. . |
| 0 530160 | 3/1993 | European Pat. Off. . |
| 3043336 | 11/1981 | Germany . |
| 332486 | 2/1971 | Sweden . |
| 1 291 470 | 10/1972 | United Kingdom . |

OTHER PUBLICATIONS

Langer et al., "The Wide Fixture: A Solution for Special Bone Situations and a Rescue for the Compromised Implant. Part 1," The International Journal of Oral & Maxillofacial Implants, pp. 400–408, vol. 8, No. 4, 1993 (9 pages).

Academy of Osseointegration Program, Mar. 4–6, 1993, cover page and pp. 32–33.

U. Lekholm, "The Branemark Implant Techniques: A Standardized Procedure Under Continuous Development," 2nd Int. Tissue International Congress, Rochester, Minnesota, Sep. 1990, pp. 194–199.

Jaffin & Berman "The Excessive Loss of Branemark Fixtures in Type IV Bone: A 5-Year Analysis," J. Peridontal, 1991, 62:2–4.

Langer, B. et al., "Osseointegration: Its Impact On The Interrelationship of Peridontics And Restorative Denistry: Part 1", The International Journal of.Peridontics & Restorative Dentistry, vol. 9, No. 2, 1989 at pp. 85–105.

Core-Vent Corporation "Spectra System: The Only Complete System of Osseointegrated Implants", 1990.

Core-Vent Corporation "Diagnosis And Treatment Planning Guidelines", Oct. 12, 1989.

Core-Vent "Les Systemes Implantaires", Jan. 10, 1990.

(List continued on next page.)

*Primary Examiner*—Cary E. O'Connor

[57] ABSTRACT

A dental implant fixture intended for installation in maxillary and mandibular posterior regions where bone is cancellous internally and cortical externally characterized by labial and lingual cortical plates bounding a relatively large body of cancellous bone. The body of the implant fixture has a width dimension that is substantially the same as the distance between the labial and lingual cortical plates in the site of installation and has a stop flange of substantially the same width at its gingival end. When the implant is installed in that site the stop flange makes bone-to-implant contact with the coronal bone which joins the plates. The length of this implant fixture is limited so that when so installed it does not make contact with the mandibular canal or the sinus cavity.

150 Claims, 4 Drawing Sheets

U.S. PATENT DOCUMENTS

| | | | |
|---|---|---|---|
| 3,846,846 | 11/1974 | Fischer . | |
| 4,145,764 | 3/1979 | Suzuki et al. . | |
| 4,414,966 | 11/1983 | Stednitz . | |
| 4,424,037 | 1/1984 | Ogino et al. | 433/173 |
| 4,463,753 | 8/1984 | Gustilo . | |
| 4,466,796 | 8/1984 | Sandhaus | 433/173 |
| 4,468,200 | 8/1984 | Münch | 433/174 |
| 4,480,997 | 11/1984 | Deutsch et al. | 433/221 |
| 4,484,570 | 11/1984 | Sutter et al. . | |
| 4,495,664 | 1/1985 | Blanquaert . | |
| 4,511,335 | 4/1985 | Tatum, Jr. | 433/173 |
| 4,535,487 | 8/1985 | Esper et al. | 623/22 |
| 4,537,185 | 8/1985 | Stednitz . | |
| 4,668,191 | 5/1987 | Plischka | 433/174 |
| 4,713,003 | 12/1987 | Symington et al. | 433/173 |
| 4,713,004 | 12/1987 | Linkow et al. | 433/174 |
| 4,722,688 | 2/1988 | Lonca | 433/173 |
| 4,738,623 | 4/1988 | Driskell | 433/173 |
| 4,790,753 | 12/1988 | Fradera | 433/174 |
| 4,793,808 | 12/1988 | Kirsch | 433/173 |
| 4,826,434 | 5/1989 | Krueger | 433/174 |
| 4,846,683 | 7/1989 | Lazzara et al. | 433/173 |
| 4,851,008 | 7/1989 | Johnson | 623/16 |
| 4,854,872 | 8/1989 | Detsch | 433/133 |
| 4,863,383 | 9/1989 | Grafelmann | 433/174 |
| 4,878,915 | 11/1989 | Brantigan | 623/17 |
| 4,915,628 | 4/1990 | Linkow et al. | 433/173 |
| 4,932,868 | 6/1990 | Linkow et al. | 433/174 |
| 4,934,935 | 6/1990 | Edwards | 433/173 |
| 4,955,811 | 9/1990 | Lazzara et al. | 433/173 |
| 4,960,381 | 10/1990 | Niznick | 433/174 |
| 4,978,350 | 12/1990 | Wagenknecht | 606/72 |
| 4,988,299 | 1/1991 | Branemark | 433/174 |
| 5,015,186 | 5/1991 | Detsch | 433/173 |
| 5,026,280 | 6/1991 | Dürr et al. | 433/173 |
| 5,049,073 | 9/1991 | Lauks | 433/173 |
| 5,061,181 | 10/1991 | Niznick | 433/174 |
| 5,064,425 | 11/1991 | Brånemark et al. | 606/72 |
| 5,076,788 | 12/1991 | Niznick | 433/173 |
| 5,078,607 | 1/1992 | Niznick | 433/174 |
| 5,100,323 | 3/1992 | Friedman et al. | 433/173 |
| 5,135,394 | 8/1992 | Hakamatsuka et al. | 433/173 |
| 5,188,800 | 2/1993 | Green, Jr. et al. | 422/23 |
| 5,205,745 | 4/1993 | Kamiya et al. | 433/173 |
| 5,209,659 | 5/1993 | Friedman et al. | 433/173 |
| 5,254,005 | 10/1993 | Zuest | 433/173 |
| 5,269,685 | 12/1993 | Jörnéus et al. | 433/174 |
| 5,312,256 | 5/1994 | Scortecci . | |
| 5,324,199 | 6/1994 | Branemark | 433/174 |
| 5,435,723 | 7/1995 | O'Brien | 433/174 |
| 5,449,291 | 9/1995 | Lueschen et al. | 433/173 |
| 5,591,029 | 1/1997 | Zuest | 433/174 |

OTHER PUBLICATIONS

Driskell Bioengineering, "The DB Precision Implant System 1000 Series", 1986.

"Cemented Abutments for Crown and Bridge", Date Prior to Filing Date.

Core–Vent Corporation "Order Form", Sep. 1989.

Core–Vent Corporation "The Longitudinal Clinical Efficacy of Core–Vent Dental Implants: A Five–year Study", Journal of Oral Implantology, vol. XV, No. 2, 1989.

Ledermann, Frischherz, and Markwalder, "The Ha–Ti Implant", Schweiz Monatsschr Zahnmed, vol. 101, May 1991.

Bone Screw Technical Information by Richards Technical Publication (1980, pp. 1–14).

Sustain®, H–A Bointegrated Dental Implant System, 1991.

Steri–Oss, The Future of Implant Dentistry, 1990.

OsteoImplant Corp., 1990.

Southern Implants, B–Series Dental Implants, Apr. 1, 1993.

Interpore, Price and Data Sheet, 1989.

Imtec, Hexed Head Implant Systems, Spring 1993 Catalog, 1993.

Implant Support Systems, Inc., Products for diagnosis, surgery, restoration, laboratory, 1989.

Implamed, The Source, Nov. 1992.

Dentsply, Restorative Manual, 1992.

Dentsply, Price List, Jun. 1, 1992.

"Ha–Ti Implant Short Neck Measuring Template," Mathys Dental LTD, Aug. 1992.

"Titanodont™ Subcortical Implant System," Miter, Inc.

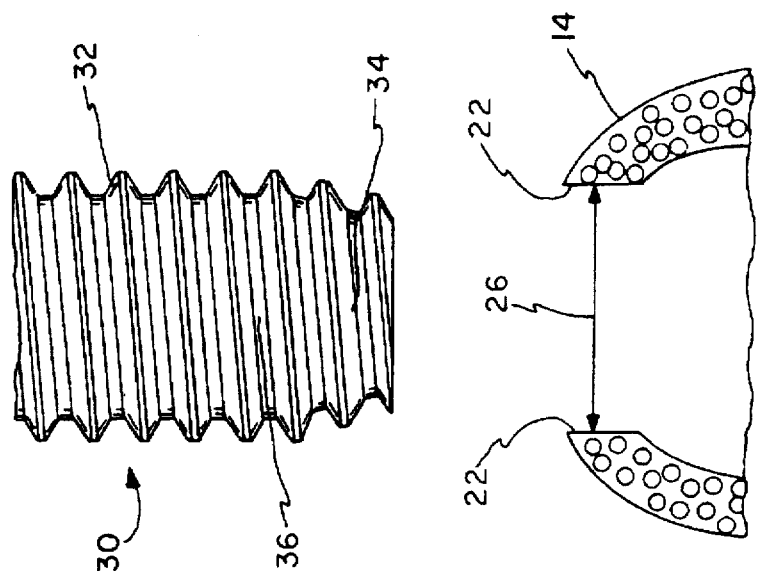
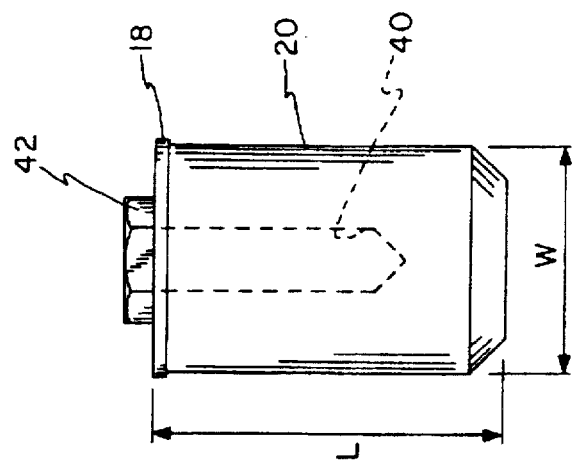
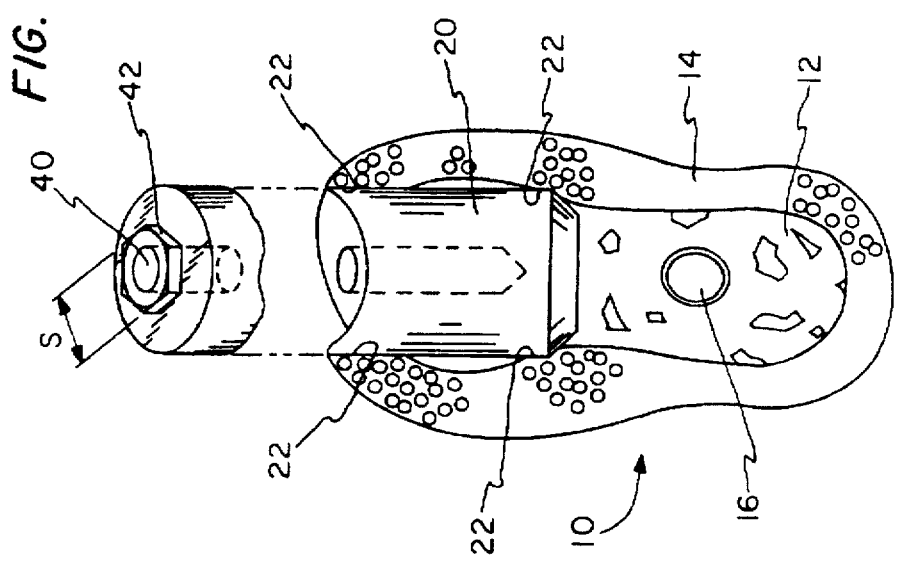

DENTAL IMPLANT FIXTURE FOR ANCHORAGE IN CORTCAL BONE

This is a continuation of Application Ser. No. 08/222,928, filed Apr. 5, 1994, now abandoned, which is a continuation application of application Ser. No. 07/845,138, now U.S. Pat. No. 5,364,268, filed Mar. 3, 1992.

BACKGROUND OF THE INVENTION

This invention relates to dental implant fixtures, particularly to fixtures intended for installation in the maxillary and mandibular posterior regions where bone is cancellous internally and cortical externally.

As it has developed to the present time, the technology of dental implant fixtures preferentially employs cylindrical implant fixtures, some externally threaded, and some not so threaded, but all being much longer than they are wide with the ratio of length to width being about 1.8 to 5.3, for example. This may be due primarily to the fact that early successes were experienced with installation in the anterior area of dental arches, using dental implant fixtures which have lengths ranging up to about 20 mm and widths up to about 4 mm. Predictability of this type of installation in the anterior area of dental arches is now so good that the use of dental implant fixtures has entered the armamentarium of oral surgeons, prosthodontists and periodontists in the treatment of fully and partially edentulous patients. Attempts to install dental implant fixtures in posterior regions of the maxillary and mandibular arches have, however, encountered several unique problems.

On the one hand, such attempts have been frustrated by the presence of the inferior alveolar nerve chamber (mandibular canal) in posterior mandible, and by the presence of the sinus cavities superior to the posterior maxillary bone crest. Risk of invading the sinus cavities and the mandibular canal is generally avoided, the result being that often in these posterior regions no more than about 8 mm or less of bone depth is available in which to prepare a bore to receive a dental implant fixture. Therefore, very shod implants were placed with less square millimeters of surface area in bone for foundation. Lekholm reported reduced success with shorter implants. (2nd Int. Tissue International Congress, Rochester, Minn., September, 1990). In order to place longer implant fixtures in these regions, many surgeons have resorted to more aggressive surgical techniques, including sinus lift procedures and mandibular nerve repositioning procedures. These procedures are obviously of greater risk than standard implant treatment in the anterior regions of the mouth. It is an advantage of the present invention to avoid these procedures. Some practitioners have sought to overcome this problem in the mandible, if the mandibular canal is located in a buccal position, by installing an available denial implant fixture closer to the lingual surface, and thereby bypassing the mandibular canal, when adequate bone is available to the lingual surface to avoid the risk of fenestration. This procedure, when available, may have the advantage of providing partial primary stabilization in cortical bone, which is important for eventual osseointegration of the fixture with the bone.

It has become apparent that wider jawbones (as in the posterior regions) usually have more trabeculation and often are without adequate amounts of density of bone in their marrow spaces to provide anchorage for dental implant fixtures. In the maxillary and mandibular posterior regions the bone is cancellous internally and cortical externally, a condition sometimes termed "eggshell". It has been found to be often almost impossible to securely immobilize a dental implant fixture in the marrow spaces of posterior jawbone regions. Jaffin & Berman noted less success in bone in posterior regions. J. Periodontal, 1991, 62: 2–4. It has been suggested that the only hope of more predictable success in these cases is to place a dental implant fixture so as to engage a denser, more cortical layer of bone that often protects the maxillary and nasal sinuses, or that covers the mandibular canal, or engaging buccal-lingual plates in the posterior mandible or maxilla, all of which have inherent surgical risk.

The above-described difficulties and proposed solutions are presented in greater detail in an article by Langer, B. et al entitled "Osseointegration: Its impact on the Interrelationships of Periodontics and Restorative Dentistry: Part 1: The International Journal of Periodontics & Restorative Dentistry, Volume 9, Number 2, 1989, at pages 85 to 105.

GENERAL NATURE OF THE INVENTION

In accordance with the present invention a dental implant fixture having a cylindrically-shaped post portion which is preferably not more than about 13 mm long has a diameter preferably large enough (about 5 or 6 mm) to make bone-to-implant contact with cortical bone at both the lingual and buccal sides of posterior "eggshell" jawbone and includes stop means at its gingival end so that it can be installed without coming into contact with either the mandibular canal or the sinus floor. This new implant fixture has several advantages:

a—it has a length-to-width ratio in a range from about 0.833 to about 2.5 in dimensions providing bilateral bone-to-implant contact and a positive stop enabling installation without making contact with the mandibular canal or the sinus floor;

b—by contacting cortical bone at both sides of the bore in the jawbone and including a positive gingival stop at the superior cortex it provides more complete initial stabilization to the installed dental implant fixture; Langer et al., at page 89, show an installation in which a standard prior-existing long thin implant fixture is located to engage lingual cortical plate to provide initial stabilization, which obviously does not provide this advantage; the installation is in an unfavorable position for the construction of a fixed prosthesis;

c—owing to its larger width and gingival stop it provides a more stable platform for molar restorations than is available from the prior existing narrower implant fixtures, as well as larger surface area of an implant contact with bone, which results in smaller actual stresses in the bone-implant interface under a given occlusal load; these advantage are also lacking in Langer et al. Although the reaction of bone to stresses imposed by occlusal loading on implant fixtures is not well known and understood, it appears reasonable that any loading in the posterior regions of the mouth where cancellous bone is prevalent would benefit from a wider distribution of these stresses in the cortical bone.

d—non-circular (e.g.: hexagonal) manipulative and non-rotational devices now in use can be made wider to improve manipulation of the fixture and stabilization of restorations, especially single-tooth crowns, supported on them. In the existing state of the art of dental implants, the ratio of the width of the non-rotating feature to the total diameter of the implant is in a range of approximately 0.7 to 0.8 mm. Maintaining this same ratio in a larger diameter implant (5 or 6 mm in diameter, for example) makes it possible to utilize a much larger dimension in the non-rotational features of the implant.

This larger dimension and positive gingival step when used in conjunction with prosthetic components that have similar clearances or fit allowances between them as currently exist in the state of the art, provides for a much more stable interlocking mechanism. Essentially this revolves around the concept of retaining a minimum gap or fit between two components, but increasing the relative sizes of both of these components. By doing so, one allows the state of the art in existing manufacturing to be easily utilized to accomplish a more stable restoration when utilizing a larger diameter in the non-rotational dimensions of the components. By way of simple illustration, if one imagines a one-thousandth of an inch gap between an abutment and an implant fixture given the current state of the art, there will be a certain amount of play or micro movement between the prosthetic components and the implant fixture. If one can double the size of the non-rotational fitting, while still maintaining the same one-thousandth of an inch gap, the relative amount of motion or micro-movement between the prosthetic components and the implant fixture will decrease accordingly. The reduction of this relative motion is of significant advantage in keeping prosthetic components tight, particularly when used in single tooth applications.

In addition to the advantages offered by increased width of non-rotating fittings, the opportunity to increase the height or depth of such fittings may also offer significant advantages, particularly in single tooth restorations. The stability of the screw joint complex in single tooth restorations in the molar region is more important than in other regions of the mouth because of increased occlusal loads in this area. The addition of wider non-rotating features and taller or deeper non-rotating features, such as higher hexes or deeper hex sockets, will increase the integrity of the screw joint complex thereby reducing problems associated with micro movement and screw loosening.

e—Its larger size has advantages with regard to the final restoration and tooth emergence profile. Particularly in the posterior regions of the mouth where molars may be replaced, a larger diameter emergence profile may be desirable. This is particularly true in single tooth applications where it is important to preserve the emergence profile of a natural tooth in order to maintain subgingival contours which are easily cleaned and do not function as traps for debris and food. To create such tooth emergence profiles with smaller diameter implant fixtures often requires procedures such as ridge lapping or lingual bulking of restorative materials which makes hygiene very difficult. In anterior regions of the mouth it is often possible to overcome the shortcomings of narrower diameter implants by placing the implant more apically in the restored ridge. This allows for gradual contouring of the restoration subgingivally and can result in a more natural tooth emergence profile. However, in the posterior regions of the mouth this is often not practical because of limitations in anatomy which have been mentioned previously.

These and other advantages and features of the invention will become apparent from the following description of exemplary embodiments of the invention with reference to the accompanying drawings.

BRIEF DESCRIPTION OF THE DRAWINGS

FIG. 1 is a schematic view of the cross-section of a mandibular posterior region with a dental implant fixture of the invention installed;

FIG. 1A is a schematic top view of FIG. 1;

FIG. 2 illustrates schematically a dental implant fixtures according to the invention;

FIG. 3 is a partial side view of an externally-threaded dental implant fixture;

DETAILED DESCRIPTION OF THE DRAWINGS

Figure 5:
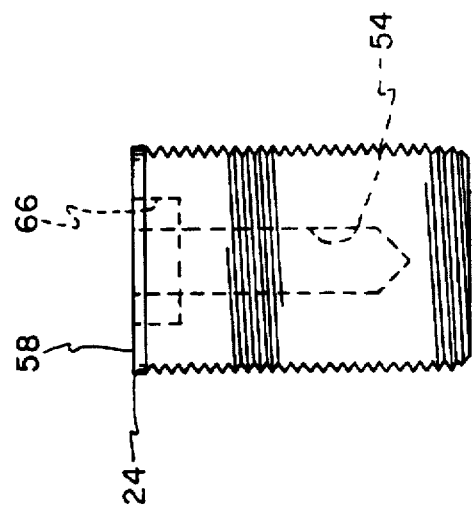
FIG. 5 is a side view of another dental implant fixture shown schematically.

FIG. 1 schematically represents a posterior region 10 of a mandible, showing a typical eggshell configuration which is cancellous internally 12 and cortical externally 14. The mandibular canal 16 is in the cancellous portion of the mandible. A dental implant fixture 20 (shown more completely in FIG. 2) is installed in the mandible making full contact with coronal bone (superior cortex) and partial bone-to-implant contact with the lingual and buccal cortical walls 14 at locations labelled 22. Owing to the "egg-shell" condition existing in this region, the coronal opening into the jawbone is not countersunk, so as to maximize the area of the contact locations 22. For the most part, the implant fixture displaces cancellous bone 12. The coronal bone-to-implant contact, and lingual and buccal partial contacts 22 provide near-total initial stabilization to the implant at both the lingual and the buccal sides of the mandible.

Referring now to FIG. 2, the implant fixture 20 of this invention is generally cylindrical in form, and has length L and width W dimensions which are unique and unlike the dimension of typical implant fixtures that are in regular current use. That width dimension W is not less than about 4.5 mm, and is preferably 5.0 mm to 6.0 mm. The ratio L/W is a range from about 0.833 to about 2.5. For example, L may be not more than about 8 to 13 mm, while W may be up to about 7 or 8 mm, depending on the width of the jawbone at the posterior location chosen for the implant fixture. The limit on L is dictated by the location of the mandibular canal 16, which may be less than 8 or 10 mm. In contrast to these unusual dimensions, implant fixtures currently available have lengths up to about 20 mm, and widths up to about 4 mm, thus having LAN ratios as high as 4.5, for example. A dental implant fixture having this L/W ratio and limited to L not greater than about 8 to 10 mm would not be able to make bone-to-implant contact with both sides of the cortical shell in a posterior location. According to the invention, the dental implant 20 has a top flange 18 that is not substantially wider than the fixture 20, and has a thin axial dimension, like the top flange 24 that is shown in and described in greater detail with reference to FIGS. 4 and 5.

FIG. 3 shows schematically an implant fixture 30 bearing a screw thread 32 on its outer surface, for initial mechanical fixation of the implant fixture in the coronal wall and in the cortical walls 14. In accordance with this embodiment the lower or apical portion 34 of the implant body 36 may be tapered to a smaller diameter than the major portion of the implant body; both the peaks of the thread 32 and the roots of the threads taper substantially equally with the major and minor diameters parallel to each other. This feature may be used to thread an implant fixture into the opening 26 through the superior cortex in the cortical bone 14, where the contact locations 22 are not countersunk, for the reason explained above.

Figure 4A:
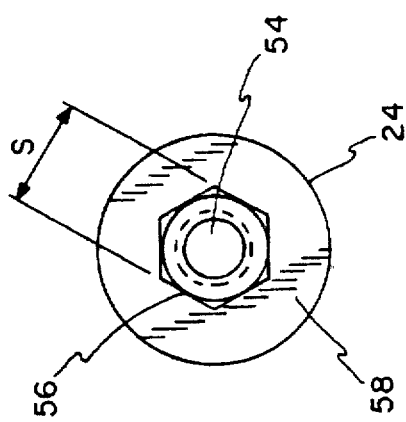
FIG. 4A is a top view of FIG. 4.
Figure 4:
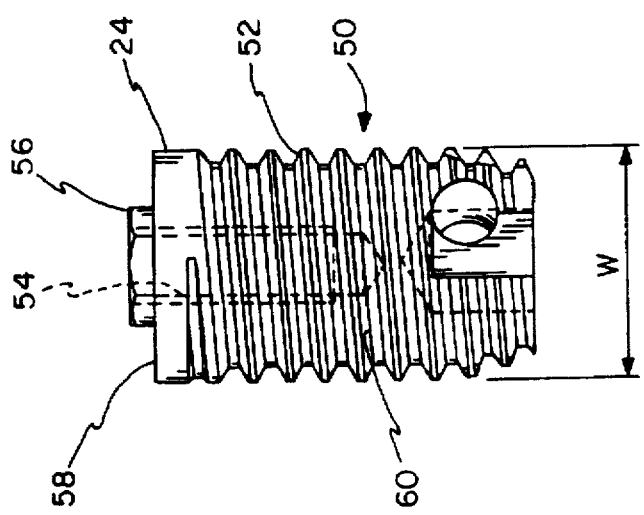
FIG. 4 is a slightly enlarged side view of an externally-threaded fixture in a form in which it may be manufactured.

FIGS. 4 and 4A show a cylindrical implant fixture 50 bearing an exterior screw thread 52 on a cylindrical body 60 of substantially uniform diameter W over its major portion (lengthwise), and tapered apically, like FIG. 3. A top flange 24 has substantially the same diameter as the peak diameter of the thread 52, and is itself without thread. The thickness of this flange 24 in the axial direction is limited to about 0.016 to about 0.020 mm up to about ¼ mm., preferably not more than about the root width of 1 to 2 adjacent turns of the thread 52. Its top to side edges are preferably sharp without burrs. This implant fixture has self-tapping features at its apical end. When it is threaded into the coronal opening 26 (see FIG. 3) the thread 52 engage coronal bone throughout the contact locations 22 and the top flange 24 is brought firmly to a stop just outside the coronal opening 26. The stop 24 may enter the coronal opening in part, where the thread ends, but should not displace the thread 52 in the opening 26.

In common with prior existing implant fixtures, the fixtures of this invention may have a receiving bore (40 in FIGS. 2 & 3; 54 in FIGS. 4 & 4A) for receiving and holding restoration components (not shown). This bore may be internally threaded as shown at 54 in FIG. 4. A non-circular (e.g: hexagonal) fitting 42 (FIG. 2), 56 (on top surface 58 of the flange 24 in FIG. 4) may be provided, externally as shown in these figures, or internally 66 as shown in FIG. 5, for the known purposes of manipulating the implant fixture and for stabilizing a restoration component against rotation with respect to the implant fixture around their common axis. The distance S between two opposite flat surfaces of this fitting may, however, be larger in the present invention than in the prior known implant fixtures, and the ratio between the width W and the dimension S can be selected to provide enhanced stabilization to the restoration components and to the restoration built on them, as is explained above in this specification.

Thus, for example, S can be greater than the usual 3 mm, while W can be up to about 10 mm. A dimension of S at 4 mm is closer to the diameter of a posterior tooth, and therefore more stabilizing. This yields a ratio of W/S that is about 2.5. If S is still larger, this ratio becomes smaller.

In use the externally-threaded implant fixtures of the present invention are installed in thread-engaging contact with at least the coronal bone, and preferably with both cortical walls 14, and the thin stop flange 24 engages the outer surface of the coronal bone to prevent insertion of the implant fixture beneath the superior cortex and possible contact with the mandibular canal. Countersinking of the coronal bone is not necessary, and should be avoided.

Wide diameter dental implants according to the invention provide an advantage in regenerative procedures. In the sinus graft area the larger diameter implant in the sinus graft reduces the amount of graft material which is necessary in order to fill the sinus for regeneration. In addition, in the extraction site, the large diameter implant fills the socket more and therefore requires less regeneration within the socket. Bone cells moving from the bone marrow have less distance to travel to reach the implant surface to regenerate bone and new osseointegrated surface.

Figure 8:
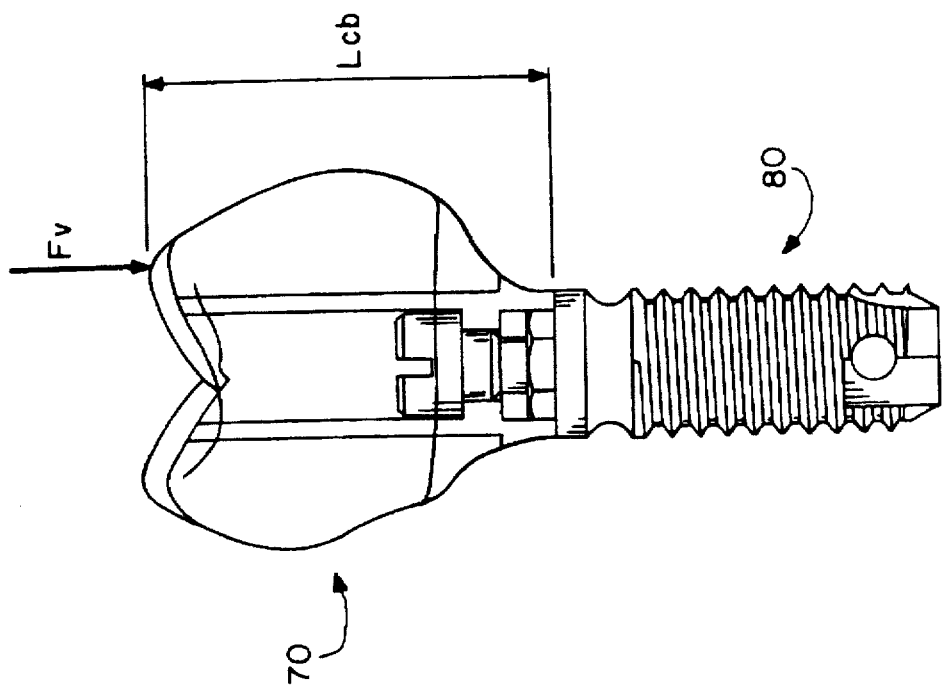
FIG. 8. illustrates the destructive dynamic forces imposed by the prior art.

Prosthetically, the unique design of the wide diameter dental implant according to the invention allows the support for the prosthesis to be brought out under the cusps of the teeth. This provides increased resistance to tipping forces and reduces stress on the abutment screw. Coordinated impression coping (not shown) can transfer the wider (e.g: 5 or 6 mm) dimension to the laboratory model so that a good emergence profile is developed and the support extends out substantially under the cusps of the teeth. Since maxillary and mandibular first molar teeth have approximately 6 mm from cusp tip to cusp tip buccal-lingually, a large diameter dental implant according to the invention will better withstand the occlusal loading since the shoulder of the implant comes out under those cusps tips. In the anterior bicuspid regions large diameter implants also provide better stability for these teeth, as well as developing better emergence profile. These advantages are illustrated in FIGS. 6, 7 and 8 of the drawings.

Figure 6:
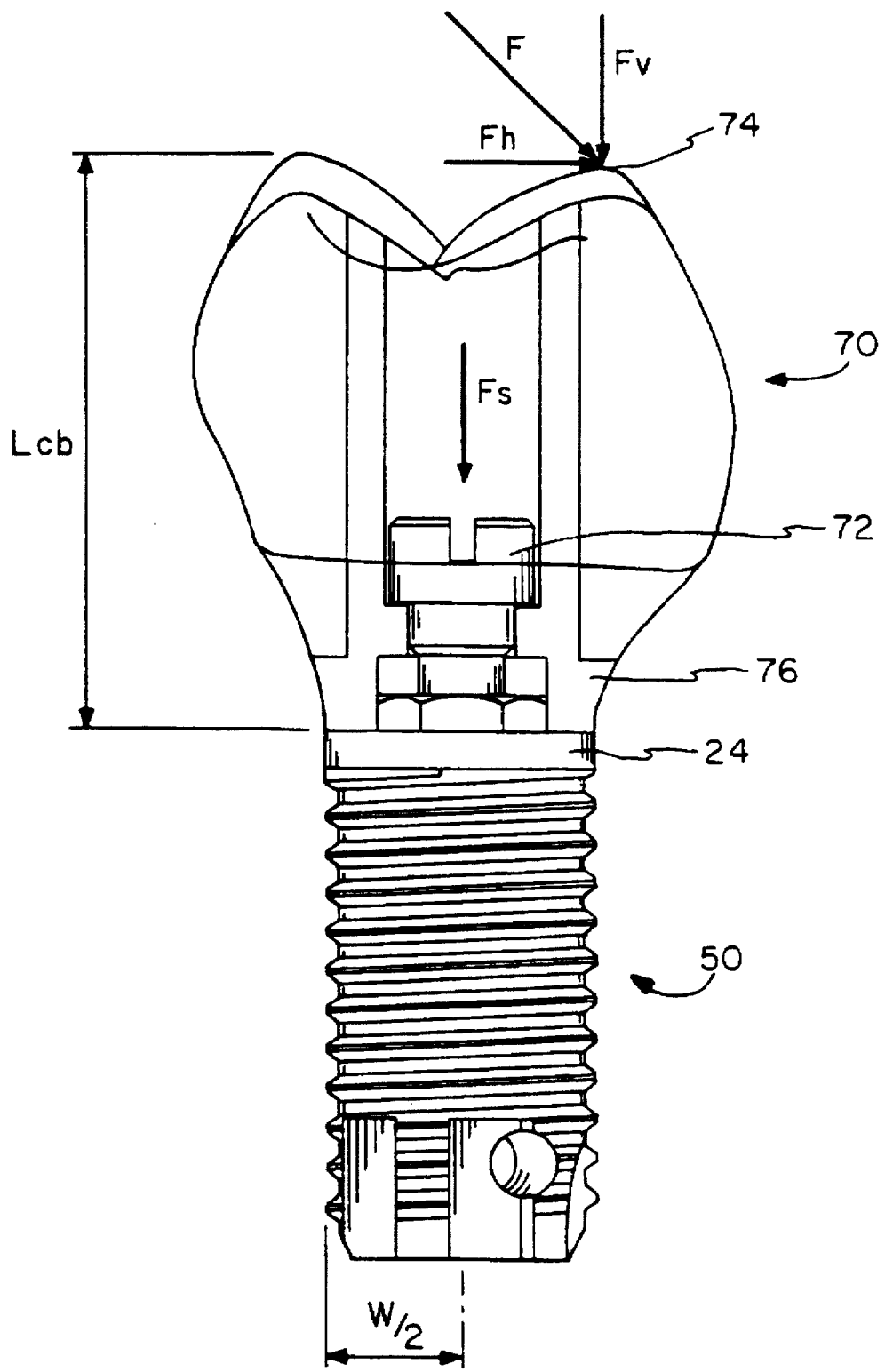
FIG. 6 shows an artificial tooth affixed to a dental implant.
Figure 7:
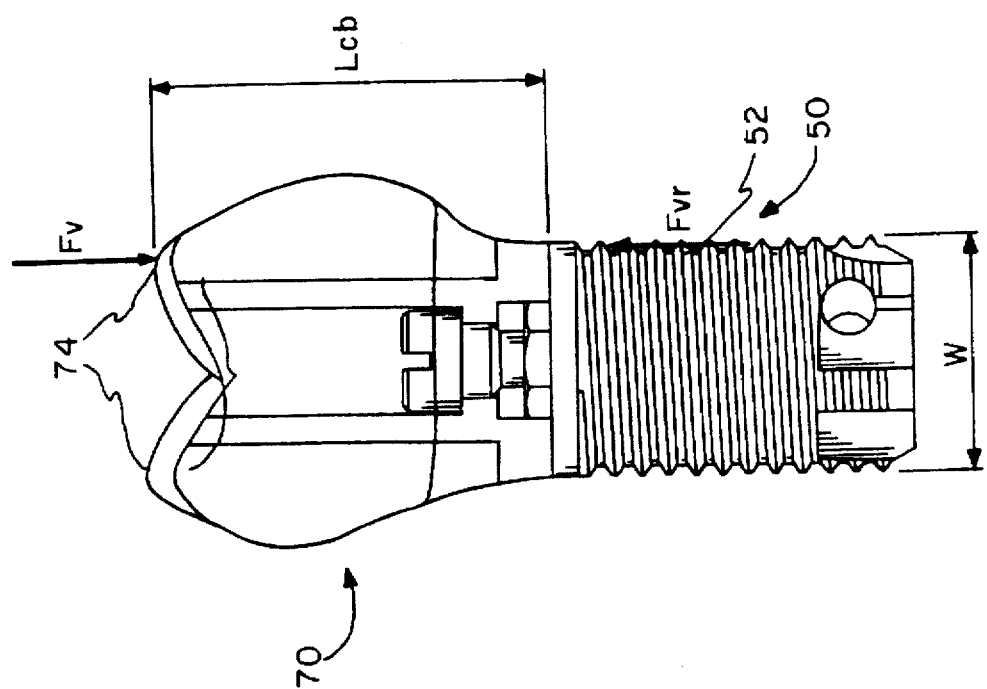
FIG. 7 is like FIG. 6, marked to illustrate improved dynamic forces made possible by the invention.

FIG. 6 shows an artificial tooth 70 of known form affixed to the dental implant 50 by means of an abutment screw 72 that is under a prescribed static installed tension. According to the invention, the abutment 76 on which the tooth 70 is formed has a wide base having a meeting surface in contact with the top flange 18 or 24 and of substantially the same shape and diameter as the flange 18 or 24 and the implant 20 or 50, respectively. An analysis of the forces generated on the abutment screw due to mastication, for example, finds that a dental restoration made on the wide implant of the present invention benefits significantly relative to a similar restoration made on the narrower implants of the prior art.

In FIG. 6:

$F$=occlusal force on the tooth 70 applied at an angle which is generally normal to the surface of a cusp 74

$Fv$=vertical components of the occlusal force $Fh$=horizontal or lateral component of the occlusal force $Fs$=incremental tension in the abutment screw 72 resulting from Fh $Lcb$=length of crown plus its abutment $W/2$=one-half the diameter of the implant 50

The incremental tension Fs on the abutment screw 72 relative to the horizontal load Fh is defined in the relation:

$$Fh \times Lcb = Fs \times W/2$$

from which:

$$Fs = \frac{Fh \times Lcb}{W/2}$$

Thus, as W/2 becomes larger Fs becomes smaller. A dental restoration according to the present invention using wide implants and wide-base abutments with matching diameters of 5.00 mm or larger will put smaller incremental tension on the abutment screw 72 than would restorations made according to the prior art, given the same or similar horizontal load on the tooth. This improvement is illustrated with the aid of FIGS. 7 and 8.

In FIG. 7 the vertical component of force, Fv, bearing on cusp 74, generates a reactionary force component Fvr directly below it, substantially at or within the threads 52, at the boundary between the implant fixture and the host bone 14 (not shown in FIG. 7). There is little or no incremental tension Fs developed, and little or no tendency to twist the implant fixture in the bone.

In FIG. 8, on the other hand, where a prior art form of narrow implant fixture 80 is shown, W/2 is smaller, and the vertical component of occlusal force Fv, in a normal molar is outside the diameter of the implant fixture. This condition tends to produce greater incremental tension Fs as explained above, and it tends further to rock the implant fixture from side-to-side in its socket in the host bone. This risk is not acceptable in posterior locations, for reasons fully developed above.

We claim:

1. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

an implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm and substantially constant for a substantial portion of the distance between said apical and gingival ends; and stop means at said gingival end for stopping penetration of said gingival end beyond said superior cortical bone, said stop means including a flange with a maximum diameter that is approximately no larger than a peak-to-peak diameter of said thread on said implant body.

2. A dental implant according to claim 1, wherein said diameter of said flange is the same size as said peak-to-peak diameter of said thread on said implant body.

3. A dental implant according to claim 1, wherein an axial thickness of said flange is less than approximately an axial distance required for two adjacent turns of said thread.

4. A dental implant according to claim 1, wherein said flange is not threaded.

5. A dental implant according to claim 1, wherein said width dimension W is about 5.5 mm.

6. A dental implant according to claim 1, wherein said width dimension W is about 6.0 mm.

7. A dental implant according to claim 1, wherein said apical end of said implant body includes a self-tapping region with a diameter less than said width dimension W.

8. A dental implant according to claim 1, wherein said length dimension L is in the range from about 8.0 mm to about 13.0 mm.

9. A dental implant according to claim 1, wherein said implant body has said thread substantially along said length dimension L.

10. A dental implant according to claim 1, wherein an apical portion of said implant body tapers toward said apical end.

11. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

a unitary implant body having a gingival end to be located in a gingival region of said jawbone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm and a minimum axial distance between adjacent surfaces on at least one pair of successive turns of said thread being approximately no larger than the maximum axial thickness of said thread; and stop means at said gingival end for stopping said gingival end from penetrating through said superior cortical bone, said stop means including a flange with a diameter that is larger than a minor diameter of said thread on said implant body.

12. A dental implant according to claim 11, wherein said diameter of said flange is approximately the same size as a peak-to-peak diameter of said thread on said implant body.

13. A dental implant according to claim 11, wherein an axial thickness of said flange is less than approximately an axial distance required for two adjacent turns of said thread.

14. A dental implant according to claim 11, wherein said flange is not threaded.

15. A dental implant according to claim 11, wherein said width dimension W is about 6.0 mm.

16. A dental implant according to claim 11, wherein said apical end of said implant body includes a self-tapping region with a diameter less than said width dimension W.

17. A dental implant according to claim 11, wherein said length dimension L is in the range from about 8.0 mm to about 13.0 mm.

18. A dental implant according to claim 11, wherein said width dimension W is about 5.5 mm.

19. A dental implant according to claim 11, wherein said implant body has said thread substantially along said length dimension L.

20. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

a unitary implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm;

a flange with a maximum diameter that is approximately no larger than a peak-to-peak diameter of said thread on said implant body; and a manipulating fitting on an upper surface of said flange, said manipulating fitting having a height measured from said upper surface, said height being approximately the same as an axial thickness of said flange.

21. A dental implant according to claim 20, wherein said upper surface of said flange has a substantially circular periphery.

22. A dental implant according to claim 20, wherein said manipulating fitting includes a hexagonal boss extending from said upper surface.

23. A dental implant according to claim 22, wherein said hexagonal boss has a boss diameter measured between two opposing sides of the six sides, said boss diameter being in the range from about 3.0 mm to about 4.0 mm.

24. A dental implant according to claim 20, wherein said width dimension W is about 6.0 mm.

25. A dental implant according to claim 20, wherein said apical end of said implant body includes a self-tapping region with a diameter less than said width dimension W.

26. A dental implant according to claim 20, wherein said length dimension L is in the range from about 8.0 mm to about 13.0 mm.

27. A dental implant according to claim 20, wherein said width dimension W is about 5.5 mm.

28. A dental implant according to claim 20, wherein said axial thickness of said flange is less than approximately the axial distance required for two adjacent turns of said thread on said implant body.

29. A dental implant according to claim 20, wherein said maximum diameter is at said upper surface of said flange.

30. A dental implant according to claim 20, wherein said implant body has said thread substantially along said length dimension L.

31. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:
a unitary implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm and substantially constant for a substantial portion of the distance between said apical and gingival ends;
a flange with a maximum diameter that is approximately no larger than a peak-to-peak diameter of said thread on said implant body; and
a manipulating fitting on an upper surface of said flange, said manipulating fitting having a height measured from said upper surface, said height being less than an axial thickness of said flange.

32. A dental implant according to claim 31, wherein said upper surface of said flange has a substantially circular periphery.

33. A dental implant according to claim 31, wherein said manipulating fitting includes a hexagonal boss extending from said upper surface.

34. A dental implant according to claim 33, wherein said hexagonal boss has a boss diameter measured between two opposing sides of the six sides, said boss diameter being in the range from about 3.0 mm to about 4.0 mm.

35. A dental implant according to claim 31, wherein said width dimension W is approximately 6.0 mm.

36. A dental implant according to claim 31, wherein said apical end of said implant body includes a self-tapping region with a diameter less than said width dimension W.

37. A dental implant according to claim 31, wherein said length dimension L is in the range from about 8.0 mm to about 13.0 mm.

38. A dental implant according to claim 31, wherein said width dimension W is about 5.5 mm.

39. A dental implant according to claim 31, wherein said axial thickness of said flange is less than approximately the axial distance required for two adjacent turns of said thread on said implant body.

40. A dental implant according to claim 31, wherein said maximum diameter is at said upper surface of said flange.

41. A dental implant according to claim 31, wherein said implant body has said thread substantially along said length dimension L.

42. A dental implant according to claim 31, wherein an apical portion of said implant body tapers toward said apical end.

43. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:
a unitary implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm and substantially constant for a substantial portion of the distance between said apical and gingival ends;
a flange with a maximum diameter that is approximately no larger than a peak-to-peak diameter of said thread on said implant body; and
a manipulating fitting on an upper surface of said flange, said manipulating fitting having a height measured from said upper surface, said height being greater than an axial thickness of said flange.

44. A dental implant according to claim 43, wherein said upper surface of said flange has a substantially circular periphery.

45. A dental implant according to claim 43, wherein said manipulating fitting includes a hexagonal boss extending from said upper surface.

46. A dental implant according to claim 45, wherein said hexagonal boss has a boss diameter measured between two opposing sides of the six sides, said boss diameter being in the range from about 3.0 mm to about 4.0 mm.

47. A dental implant according to claim 43, wherein said width dimension W is about 6.0 mm.

48. A dental implant according to claim 43, wherein said apical end of said implant body includes a self-tapping region with a diameter less than said width dimension W.

49. A dental implant according to claim 43, wherein said length dimension L is in the range from about 8.0 mm to about 13.0 mm.

50. A dental implant according to claim 43, wherein said width dimension W is about 5.5 mm.

51. A dental implant according to claim 43, wherein said axial thickness of said flange is less than approximately the axial distance required for two adjacent turns of said thread on said implant body.

52. A dental implant according to claim 43, wherein said maximum diameter is located at said upper surface of said flange.

53. A dental implant according to claim 43, wherein said implant body has said thread substantially along said length dimension L.

54. A dental implant according to claim 43, wherein an apical portion of said implant body tapers toward said apical end.

55. A set of dental implants for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said set comprising a plurality of dental implants, each of said dental implants including, an implant body having a gingival end to be located near said superior cortical bone and an apical end to be located within said jawbone a length dimension L from said gingival end, said implant body having at least one thread and a width dimension W that is substantially constant for a substantial portion of the distance between said apical and gingival ends;

stop means at said gingival end for stopping penetration of said gingival end beyond said superior cortical bone, said stop means including a flange with a diameter that is larger than a minor diameter of said at least one thread on said implant body, and a manipulating fitting on an upper surface of said flange, said manipulating fitting having a fitting width measured across said upper surface, wherein at least one of said plurality of implants has a width dimension W less than approximately 4.0 mm and at least a second one of said plurality of implants has a width dimension W at least about 5.0 mm, said fitting width of each of said implants being substantially the same.

56. A set of dental implants according to claim 55, wherein said second one of said plurality of implants has an implant body with a width dimension W in the range from about 5.5 mm to about 6.0 mm.

57. A set of dental implants according to claim 55, wherein said length dimension L of said first and second ones of said plurality of implants is approximately the same.

58. A set of dental implants according to claim 55, wherein said stop flanges of said first and second ones of said plurality of implants are approximately the same as a peak-to-peak diameter of said at least one thread.

59. A set of dental implants according to claim 55, wherein said upper surfaces of said first and second ones of said plurality of implants have different diametric dimension.

60. A set of dental implants according to claim 55, wherein said implant bodies have at least one thread substantially along said length dimension L.

61. A set of dental implant according to claim 55, wherein an apical portion of said implant body of each of said dental implants of said set tapers toward said apical end.

62. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

an implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm;

a flange with a maximum diameter that is approximately no larger than a peak-to-peak diameter of said thread on said implant body; and a manipulating fitting on an upper surface of said flange, said manipulating fitting having a height measured from said upper surface, said height being approximately the same as the distance measured from the periphery of said upper surface to said manipulating fitting.

63. A dental implant according to claim 62, wherein said upper surface of said flange has a substantially circular periphery.

64. A dental implant according to claim 62, wherein said manipulating fitting includes a hexagonal boss extending from said upper surface.

65. A dental implant according to claim 64, wherein said hexagonal boss has a boss diameter measured between two opposing sides of the six sides, said boss diameter being in the range from about 3.0 mm to about 4.0 mm.

66. A dental implant according to claim 62, wherein said width dimension W is about 6.0 mm.

67. A dental implant according to claim 62, wherein said apical end of said implant body includes a self-tapping region with a diameter less than said width dimension W.

68. A dental implant according to claim 62, wherein said width dimension W is approximately 5.5 mm.

69. A dental implant according to claim 62, wherein said implant body has said thread substantially along said length dimension L.

70. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

an implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm;

stop means at said gingival end for stopping penetration of said gingival end beyond said superior cortical bone, said stop means including a flange with a maximum diameter that is approximately no larger than a peak-to-peak diameter of said thread on said implant body; and a manipulating fitting on an upper surface of said flange, the distance measured from the periphery of said upper surface to said manipulating fitting being approximately the same as an axial thickness of said flange.

71. A dental implant according to claim 70, wherein said upper surface of said flange has a substantially circular periphery.

72. A dental implant according to claim 70, wherein said manipulating fitting includes a hexagonal boss extending from said upper surface.

73. A dental implant according to claim 72, wherein said hexagonal boss has a boss diameter measured between two opposing sides of the six sides, said boss diameter being in the range from about 3.0 mm to about 4.0 mm.

74. A dental implant according to claim 70, wherein said width dimension W is about 6.0 mm.

75. A dental implant according to claim 70, wherein said maximum diameter is at said upper surface of said flange.

76. A dental implant according to claim 70, wherein said width dimension W is approximately 5.5 mm.

77. A dental implant according to claim 70, wherein said implant body has said thread substantially along said length dimension L.

78. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

an implant body having a gingival end to be located near said superior cortical bone and an apical end to be located within said jawbone a length dimension L from said gingival end, said implant body having a thread making multiple turns around said body and a width dimension W that is in the range from approximately 5.0 mm to approximately 6.0 mm, a portion of said thread suitable for engaging at least one of said lingual and buccal plates, a minimum axial distance measured between at least a pair of successive turns of said thread at the root thereof being approximately no larger than the maximum axial thickness of said thread;

stop means at said gingival end for stopping penetration of said gingival end beyond said superior cortical bone, said stop means including a flange with a maximum diameter that is approximately no larger than a peak-to-peak diameter of said thread on said implant body; and a manipulating fitting on an upper surface of said flange, said manipulating fitting having a fitting width measured across said upper surface through an axis of rotation of said implant body, said fitting width being approximately in the range of about 70% to about 80% of the width dimension W of said implant body.

79. A dental implant according to claim 78, wherein said manipulating fitting includes a hexagonal boss extending from said upper surface and said fitting width is measured between two opposing corners of said hexagonal boss.

80. A dental implant according to claim 78, wherein said manipulating fitting includes a hexagonal boss extending from said upper surface and said fitting width is measured between two opposing flat sides of said hexagonal boss.

81. A dental implant according to claim 78, wherein said manipulating fitting has a height, said height being approximately the same as the distance from said manipulating fitting to a periphery of said upper surface.

82. A dental implant according to claim 78, wherein said implant body has said thread substantially along said length dimension L.

83. A set of dental implants for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said set comprising a plurality of dental implants, each of said dental implants including, an implant body having a gingival end to be located near said superior cortical bone and an apical end to be located within said jawbone a length dimension L from said gingival end, said implant body having a thread making multiple turns around said body, a width dimension W, and a minimum axial distance between adjacent surfaces on successive turns of said thread being less than the maximum axial thickness of said thread, stop means at said gingival end for stopping penetration of said gingival end beyond said superior cortical bone, said stop means including a flange with a maximum diameter that is approximately no larger than a peak-to-peak diameter of said thread on said implant body, and a manipulating fitting on an upper surface of said flange, said manipulating fitting having a fitting width measured across said upper surface that is in the range of around 70% to around 80% of said width dimension W, wherein at least one of said plurality of implants has a first width W dimension that is at least approximately 5 mm, and at least one implant of said plurality of implants has a second width dimension W that is less than approximately 4.0 mm.

84. A set of dental implants according to claim 83, wherein said manipulating fitting includes a hexagonal boss extending from said upper surface and said fitting width is measured between two opposing corners of said hexagonal boss.

85. A set of dental implants according to claim 83, wherein said manipulating fitting includes a hexagonal boss extending from said upper surface and said fitting width is measured between two opposing flat sides of said hexagonal boss.

86. A set of dental implants according to claim 83, wherein said manipulating fitting has a height, said height being approximately the same as the distance from said manipulating fitting to a periphery of said upper surface.

87. A set of dental implants according to claim 83, wherein each of said implant bodies has said thread substantially along said length dimension L.

88. A set of dental components for use in mounting an artificial tooth at a site where a natural tooth is missing from a human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said set comprising:

a dental implant including
an implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm and a minimum axial distance between at least a pair of successive turns of said thread at the root thereof that is approximately no larger than the maximum axial thickness of said thread, and a flange with a maximum diameter that is approximately no larger than a peak-to-peak diameter of said thread on said implant body;

an abutment to be affixed to said dental implant for mounting said artificial tooth, said abutment having a base for engaging an upper surface of said flange, said base having a base diameter that is substantially the same as said flange diameter; and means for attaching said abutment to said dental implant.

89. A set of dental components according to claim 88, wherein said dental implant further includes a hexagonal boss on said upper surface and said abutment further includes a socket extending inwardly from said base, said socket mating with said hexagonal boss, and wherein said attaching means includes a screw having a head portion for engaging said abutment and a threaded portion for threadably engaging an internally-threaded bore in said dental implant.

90. A set of dental components according to claim 89, wherein said hexagonal boss has a boss width measured between two opposing corners of said hexagonal boss, said boss width being in the range from about 70% to about 80% of said width dimension W of said implant body.

91. A set of dental components according to claim 89, wherein said hexagonal boss has a boss width measured between two opposing flat surfaces of said hexagonal boss, said boss width being in the range from about 70% to about 80% of said width dimension W of said implant body.

92. A set of dental components according to claim 89, wherein said hexagonal boss has a boss height measured said upper surface to a distal end of said boss, said height being approximately the same as the distance from a portion of said hexagonal boss to a periphery of said upper surface.

93. A set of dental components according to claim 89, wherein said hexagonal boss has a boss height measured said upper surface to a distal end of said boss, said height being less than approximately an axial thickness of said flange.

94. A set of dental components according to claim 89, wherein said hexagonal boss has a boss height measured said upper surface to a distal end of said boss, said height being at least as large as an axial thickness of said flange.

95. A set of dental components according to claim 88, further including an impression coping for taking an impression of said site after osseointegration of said dental implant, said impression coping being adapted to fit upon and mate with said upper surface of said flange of said dental implant.

96. A set of dental components according to claim 88, wherein said artificial tooth to be mounted on said abutment includes at least two cusps, said at least two cusps being positioned within said width dimension W of said dental implant.

97. A set of dental components according to claim 88, wherein said natural tooth is a particular tooth type, said particular tooth type being of a general size that creates a gingival opening in gingiva overlying said superior cortical bone, said gingival opening having a minimum dimension not substantially larger than said width dimension W of said dental implant.

98. A set of dental components according to claim 88, wherein said width dimension W is approximately 6.0 mm.

99. A set of dental components according to claim 88, wherein said width dimension W is approximately 5.5 mm.

100. A set of dental components according to claim 88, wherein said implant body has said thread substantially along said length dimension L.

101. A set of dental components for use in mounting an artificial tooth at a site where a natural tooth is missing from a human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said set comprising:
  a dental implant including
    a unitary implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm and substantially constant for a substantial portion of the distance between said apical and gingival ends, a minimum axial distance between adjacent surfaces on at least a pair of successive turns of said thread being approximately no larger than the maximum axial thickness of said thread,
    a manipulating fitting on said gingival end with a fitting width of about 70% to about 80% of said width dimension W, and
    a flange at said gingival end having a flange diameter greater than a minor diameter of said thread for stopping penetration of said gingival end beyond said superior cortical bone;
  an abutment to be affixed to said dental implant and for receiving said artificial tooth, said abutment having a base for engaging said dental implant near said gingival end, said base having a base diameter that is approximately the same as said width dimension W of said implant body near said apical end, said abutment having a fitting portion approximately the same size as said fitting width for mating with said manipulating fitting; and means for attaching said abutment to said dental implant.

102. A set of dental components according to claim 101, further including an impression coping for taking an impression of said site after osseointegration of said dental implant, said impression coping being adapted to fit upon and mate with said dental implant near said gingival end.

103. A set of dental components according to claim 101, wherein said artificial tooth to be mounted on said abutment includes at least two cusps, said at least two cusps being positioned within said width dimension W of said dental implant.

104. A set of dental components according to claim 101, wherein said natural tooth is a particular tooth type, said particular tooth type being of a general size that creates a gingival opening in gingiva overlying said superior cortical bone, said gingival opening having a maximum dimension not substantially larger than said width dimension W of said dental implant.

105. A set of dental components according to claim 101, wherein said width dimension W is approximately 6.0 mm.

106. A set of dental components according to claim 101, wherein said width dimension W is approximately 5.5 mm.

107. A set of dental components according to claim 101, wherein said implant has said thread substantially along said length dimension L.

108. A set of dental components according to claim 101, wherein an apical portion of said implant body tapers toward said apical end.

109. A set of dental components for use in mounting an artificial tooth at a site where a natural tooth is missing from a human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said set comprising:
  a plurality of dental implants, each of said plurality of dental implants including
    an implant body having a gingival end to be located near said superior cortical bone and an apical end to be located within said jawbone a length dimension L from said gingival end, said implant body having a thread making multiple turns around said body and a width dimension W that is substantially constant for a substantial portion of the distance between said apical and gingival ends, a minimum axial distance between adjacent surfaces on at least a pair of successive turns of said thread being approximately no larger than the maximum axial thickness of said thread; and a manipulating fitting at said gingival end, said manipulating fitting for each of said plurality of implants being substantially the same size;

stop means at said gingival end for stopping penetration of said gingival end beyond said superior cortical bone, said stop means including a flange with a flange diameter that is larger than a minor diameter of said thread on said implant body;

a plurality of abutments each of which is to be affixed to one of said plurality of dental implants, each of said plurality of abutments having a base for engaging an upper surface of said flange of said one of said plurality of dental implants, said base having a base diameter that is substantially the same as said flange diameter of said one of said plurality of dental implants, each of said plurality abutments having a fitting portion for mating with said manipulating fittings, said artificial tooth capable of being mounted on each of said plurality of abutments; and means for attaching each of said plurality of abutments to said one of said plurality of dental implants, and wherein at least one of said plurality of dental implants having said width dimension W is greater than about 5.0 mm and at least one of said plurality of abutments having a base with a base diameter that is substantially the same as said width dimension W of said at least one of said plurality of dental implants, and wherein another of said plurality of dental implants having a width dimension W less than approximately 4.0 mm and another of said plurality of abutments having a base with a base diameter that is substantially the same as said width dimension W of said another of said plurality of dental implants.

110. A set of dental components according to claim 109, wherein said at least one of said plurality of dental implants has said width dimension W less than 6.0 mm.

111. A set of dental components according to claim 109, wherein at least one of said dental implants has said thread substantially along said length dimension L.

112. A set of dental components according to claim 109, wherein an apical portion of said implant body of each of said dental implants of said set tapers toward said apical end.

113. A tooth restoration to be located at a site where a natural tooth is missing from a human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said tooth restoration comprising:

a dental implant including an implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 5.0 mm, said dental implant further including a flange with a maximum diameter that is approximately no larger than a peak-to-peak diameter of said thread on said implant body;

an abutment having a base for engaging an upper surface of said flange, said base having a base diameter that is substantially the same as said flange diameter;

an artificial tooth formed on said abutment; and means for attaching said abutment to said dental implant.

114. A tooth restoration according to claim 113, wherein said artificial tooth to be formed on said abutment includes at least two cusps, said at least two cusps being positioned approximately within said width dimension W of said dental implant.

115. A tooth restoration according to claim 113, wherein said missing natural tooth is a particular tooth type, said particular tooth type being of a general size that creates a gingival opening in gingiva overlying said superior cortical bone, said gingival opening having a minimum dimension not substantially larger than said width dimension W of said dental implant.

116. A tooth restoration according to claim 113, wherein said width dimension W is approximately 6.0 mm.

117. A tooth restoration according to claim 113, wherein said width dimension W is approximately 5.5 mm.

118. A tooth restoration according to claim 113, wherein said implant body has said thread substantially along said length dimension L.

119. A tooth restoration according to claim 113, wherein said implant further includes a manipulating fitting with a fitting width that is about 70% to about 80% of the width dimension W, said abutment having a fitting portion for mating with said manipulating fitting having a size substantially the same as said manipulating fitting.

120. A tooth restoration according to claim 119, wherein said manipulating fitting is a hexagonal boss and said fitting portion is a hexagonal socket.

121. A set of dental components for use in mounting an artificial tooth at a site where a natural tooth is missing from a human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said set comprising:

a plurality of dental implants, each of said plurality of dental implants including an implant body having a gingival end to be located near said superior cortical bone and an apical end to be located within said jawbone a length dimension L from said gingival end, said implant body having a thread making multiple turns around said body, a width dimension W that is at least 5.0 mm, and a minimum axial distance between adjacent surfaces on at least one pair of successive turns of said thread being approximately no larger than the maximum axial thickness of said thread, at least one of said implants having a different width dimension W than the remaining ones of said plurality of implants; and a flange at said gingival end for stopping penetration of said gingival end beyond said superior cortical bone, said flange having a flange diameter that is larger than a minor diameter of said thread on said implant body;

a manipulating fitting on said gingival end having a fitting width that is in the range from about 70% to about 80% of said width dimension W;

a plurality of abutments each of which is to be affixed to one of said plurality of dental implants and to hold said artificial tooth, each of said plurality of abutments having a base for engaging an upper surface of said flange of said one of said plurality of dental implants, said base having a base diameter that is substantially the same as said flange diameter of said one of said plurality of dental implants, each of said abutments including a fitting portion having a size of said fitting width for mating with said manipulating fitting; and means for attaching each of said plurality of abutments to said one of said plurality of dental implants.

122. A set of dental components according to claim 121, wherein an axial thickness of said flange is less than approximately the axial distance required for two adjacent turns of said thread.

123. A set of dental components according to claim 121, wherein said plurality of implants includes implants with at least three different width dimensions W.

124. A set of dental components according to claim 121, wherein said width dimension W of at least one of said implants is about 5.5 mm.

125. A set of dental components according to claim 121, wherein said width dimension W of at least one of said implants is about 6.0 mm.

126. A set of dental components according to claim 121, wherein said length dimension L is in the range from about 8.0 mm to about 13.0 mm.

127. A set of dental components according to claim 121, wherein said thread extends substantially along said length dimension L.

128. A set of dental components for use in mounting an artificial tooth at a site where a natural tooth is missing from a human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said set comprising:

a dental implant including
an implant body having a gingival end to be located near said superior cortical bone and an apical end to be located within said jawbone a length dimension L from said gingival end, said length dimension L being less than about 13.0 mm, said implant body having a thread making multiple turns substantially along said length dimension L of said body and suitable for engaging at least one of said lingual and buccal plates, said implant body further having a width dimension W that is at least about 5.0 mm and a minimum axial distance between adjacent surfaces on at least a pair of successive turns of said thread that is approximately no larger than the maximum axial thickness of said thread, a hexagonal manipulating fitting on said gingival end with a fitting width of about 70% to about 80% of said width dimension W, and a non-threaded flange at said gingival end having a flange diameter greater than a minor diameter of said thread for stopping penetration of said gingival end beyond said superior cortical bone, said flange having an axial thickness less than the axial distance required for two adjacent turns of said thread;

an abutment to be affixed to said dental implant and for receiving said artificial tooth, said abutment having a base for engaging said dental implant near said gingival end, said base having a base diameter that is substantially the same as said flange diameter, said abutment having a hexagonal fitting portion approximately the same size as said fitting width for mating with said manipulating fitting; and means for attaching said abutment to said dental implant.

129. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

a unitary implant body having a gingival end to be located in a gingival region of said jawbone and an apical end to be located within said jawbone a length dimension L from said gingival end, said implant body having a thread making multiple turns around said body and suitable for engaging at least one of said lingual and buccal plates, said implant body further having a width dimension W that is at least about 4.5 mm and substantially constant for a substantial portion of the distance between said apical and gingival ends; and stop means at said gingival end for stopping said gingival end from penetrating through said superior cortical bone, said stop means including a flange with a diameter that is larger than a minor diameter of said thread on said implant body, said flange having an axial thickness that is less than approximately the axial distance required for two adjacent turns of said thread.

130. A dental implant according to claim 129, wherein said implants apical end of said implant body includes a self-tapping region with a diameter less than said width dimension W.

131. A dental implant according to claim 129 further including a manipulating fitting on an upper surface of said flange, said manipulating fitting having a height measured from said upper surface, said height being less than said axial thickness of said flange.

132. A dental implant according to claim 129 further including a manipulating fitting on an upper surface of said flange, said manipulating fitting having a height measured from said upper surface, said height being greater than said axial thickness of said flange.

133. A dental implant according to claim 129 further including a manipulating fitting on an upper surface of said flange, said manipulating fitting having a height measured from said upper surface, said height being approximately the same as the distance measured from the periphery of said upper surface to said manipulating fitting.

134. A dental implant according to claim 129 further including a manipulating fitting on an upper surface of said flange, said manipulating fitting having a height measured from said upper surface, said height being approximately the same as said axial thickness of said flange.

135. A dental implant according to claim 129, wherein an apical portion of said implant body tapers toward said apical end.

136. A set of dental components for use in mounting an artificial tooth at a site where a natural tooth is missing from a human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said set comprising:

a dental implant including an implant body having a gingival end to be located near said superior cortical bone and an apical end to be located within said jawbone a length dimension L from said gingival end, said implant body having a thread making multiple turns around said body and suitable for engaging at least one of said lingual and buccal plates, said implant body further having a width dimension W that is at least about 4.5 mm and substantially constant for a substantial portion of the distance between said apical and gingival ends, a minimum axial distance between adjacent surfaces on at least a pair of successive turns of said thread being approximately no larger than the maximum axial thickness of said thread, a manipulating fitting on said gingival end with a fitting width of about 70% to about 80% of said width dimension W, and a flange at said gingival end having a flange diameter greater than a minor diameter of said thread for stopping penetration of said gingival end beyond said superior cortical bone;

an abutment to be affixed to said dental implant and for receiving said artificial tooth, said abutment having a base for engaging said dental implant near said gingival end, said base having a base diameter that is approximately the same as said width dimension W of said implant body near said apical end, said abutment having a fitting portion approximately the same size as said fitting width for mating with said manipulating fitting; and means for attaching said abutment to said dental implant.

137. A set of dental components according to claim 136, wherein an axial thickness of said flange is less than approximately the axial distance required for two adjacent turns of said thread.

138. A set of dental components according to claim 136, wherein said thread extends substantially along said length dimension L.

139. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

a generally cylindrical, unitary implant body having a gingival end to be located in a gingival region of said jawbone and an apical end to be located within said jawbone, said implant body having a width dimension W that is at least about 4.5 mm so that an outer surface of said body is suitable for engaging at least one of said lingual and buccal plates; and stop means at said gingival end for stopping said gingival end from penetrating through said superior cortical bone, said stop means including a flange with a maximum diameter that is approximately the same size as said width dimension W of said implant body.

140. A dental implant according to claim 139, wherein said implant body has a thread on said outer surface.

141. A dental implant according to claim 139, wherein said implant body has structure on said outer surface that is suitable for said engagement of at least one of said lingual and buccal plates.

142. A dental implant according to claim 139, wherein said flange is not larger than said width dimension W.

143. A dental implant according to claim 139, wherein said width dimension W is at least 5.0 mm.

144. A dental implant according to claim 143, wherein said width dimension W is about 6.0 mm.

145. A dental implant according to claim 139, further including a manipulating fitting on said gingival end with a fitting width of about 70% to about 80% of said width dimension W.

146. A dental implant for installation in a living human jawbone, said human jawbone having cancellous bone tissue internally and cortical bone tissue externally, said cortical bone tissue including lingual and buccal cortical plates joined by a superior cortical bone, said lingual and buccal cortical plates bounding said cancellous bone tissue of said jawbone and being separated by a buccal-to-lingual thickness, said implant comprising:

an implant body having a gingival end to be located in a gingival region of said jawbone and an apical end to be located within said jawbone, said implant body having a thread suitable for engaging at least one of said lingual and buccal plates and a width dimension W that is at least about 5.0 mm, said thread having multiple turns adjacent to said apical end of said body; and a stop flange with a diameter that is larger than a minor diameter of said thread on said implant body for stopping said gingival end from penetrating through said superior cortical bone.

147. A dental implant according to claim 146, wherein said flange diameter is about 6.0 mm.

148. A dental implant according to claim 147, wherein said flange diameter is not substantially larger than said peak-to-peak diameter of said thread.

149. A dental implant according to claim 147, wherein said flange is substantially cylindrical.

150. A dental implant according to claim 147, wherein said flange has an axial thickness less than approximately the axial distance required for two adjacent turns of said thread.

* * * * *

UNITED STATES PATENT AND TRADEMARK OFFICE
CERTIFICATE OF CORRECTION

PATENT NO. : 5,702,346
DATED : December 30, 1997
INVENTOR(S) : Lazzara et al

It is certified that error appears in the above-identified patent and that said Letters Patent is hereby corrected as shown below:

On the title page: Item [73] Assignee: should read --
Implant Innovations, Inc., Palm Gardens, FL.

Signed and Sealed this

Thirteenth Day of April, 1999

Attest:

Q. TODD DICKINSON

Attesting Officer

Acting Commissioner of Patents and Trademarks

Disclaimer

5,702,346 - Richard J. Lazzara, Lake Worth, Fla.; Keith D. Beaty, West Palm Beach, Fla. DENTAL IMPLANT FIXTURE FOR ANCHORAGE IN CORTICAL BONE. Patent dated Dec. 30, 1997. Disclaimer filed March 22, 1999, by the assignee, Implant Innovations, Inc.

Hereby enters this disclaimer to claims 1-150 of said patent.
*(Official Gazette,* June 22, 1999)